(12) United States Patent
Mills (10) Patent No.: US 10,682,266 B2
(45) Date of Patent: *Jun. 16, 2020

(54) ABSORBENT ARTICLE

(71) Applicant: Medline Industries, Inc., Mundelein, IL (US)

(72) Inventor: Andrew J. Mills, Mundelein, IL (US)

(73) Assignee: Medline Industries, Inc., Northfield, IL (US)

( * ) Notice: Subject to any disclaimer, the term of this patent is extended or adjusted under 35 U.S.C. 154(b) by 372 days.

This patent is subject to a terminal disclaimer.

(21) Appl. No.: 15/695,098

(22) Filed: Sep. 5, 2017

(65) Prior Publication Data

US 2017/0360627 A1 Dec. 21, 2017

Related U.S. Application Data

(63) Continuation of application No. 14/551,587, filed on Nov. 24, 2014, now Pat. No. 9,750,650, which is a
(Continued)

(51) Int. Cl.
*A61F 13/56* (2006.01)
*A61F 13/514* (2006.01)
*A61F 13/84* (2006.01)

(52) U.S. Cl.
CPC ........ *A61F 13/514* (2013.01); *A61F 13/5633* (2013.01); *A61F 13/5638* (2013.01);
(Continued)

(58) Field of Classification Search
CPC ............ A61F 13/51496; A61F 13/5622; A61F 13/5633; A61F 13/5638; A61F 13/5644; A61F 13/581; A61F 2013/5683
See application file for complete search history.

(56) References Cited

U.S. PATENT DOCUMENTS

| 688,143 A | 12/1901 | Windle |
| 1,614,239 A | 1/1927 | Hammond |

(Continued)

FOREIGN PATENT DOCUMENTS

| EP | 0570980 A1 | 11/1993 |
| EP | 1915977 A1 | 4/2008 |

(Continued)

*Primary Examiner* — Catharine L Anderson
(74) *Attorney, Agent, or Firm* — Gurr Brande & Spendlove, PLLC; Robert D. Spendlove (57) ABSTRACT

An absorbent article is disclosed. The article includes a first portion having at least two target strips located on opposite ends of the first portion, at least one visual sizing indicator positioned on the first portion of the article between the at least two target strips, the visual sizing indicator including indicia for indicating that the article is too large for a wearer, a middle portion contoured inwards such that an hourglass shape is formed, and a second portion having at least two fasteners located on opposite edges of the second portion. The absorbent article is formed of several layers including a moisture-impervious outer layer, an inner layer substantially co-extensive with the outer layer, and a filler interposed between the inner layer and the outer layer.

16 Claims, 4 Drawing Sheets

Related U.S. Application Data continuation of application No. 13/755,583, filed on Jan. 31, 2013, now Pat. No. 8,920,399, which is a continuation of application No. 12/565,562, filed on Sep. 23, 2009, now Pat. No. 8,419,703, which is a continuation of application No. 11/341,015, filed on Jan. 27, 2006, now Pat. No. 8,241,263.

(60) Provisional application No. 60/712,023, filed on Aug. 26, 2005.

(52) U.S. Cl.
CPC ........ *A61F 13/84* (2013.01); *A61F 13/51496* (2013.01); *A61F 2013/5683* (2013.01); *A61F 2013/8497* (2013.01)

(56) References Cited

U.S. PATENT DOCUMENTS

| | | |
|---|---|---|
| RE26,151 E | 1/1967 | Duncan et al. |
| 3,338,992 A | 8/1967 | Kinney |
| 3,341,394 A | 9/1967 | Kinney |
| 3,485,706 A | 12/1969 | Evans |
| 3,502,538 A | 3/1970 | Petersen |
| 3,502,763 A | 3/1970 | Hartmann |
| 3,542,615 A | 11/1970 | Dobo et al. |
| 3,612,055 A | 10/1971 | Mesek et al. |
| 3,692,618 A | 9/1972 | Carduck et al. |
| 3,802,817 A | 4/1974 | Matsuki et al. |
| 3,849,241 A | 11/1974 | Harding et al. |
| 3,860,003 A | 1/1975 | Buell |
| 3,955,575 A | 5/1976 | Okuda |
| 3,994,486 A | 11/1976 | Nystrand |
| 4,050,462 A | 9/1977 | Woon et al. |
| 4,051,853 A | 10/1977 | Egan, Jr. |
| 4,055,180 A | 10/1977 | Karami |
| 4,084,592 A | 4/1978 | Tritsch |
| 4,145,763 A | 3/1979 | Abrams et al. |
| 4,195,634 A | 4/1980 | Disalvo et al. |
| 4,205,679 A | 6/1980 | Repke et al. |
| 4,246,900 A | 1/1981 | Schroder |
| 4,251,643 A | 2/1981 | Harada et al. |
| 4,253,461 A | 3/1981 | Strickland et al. |
| 4,296,750 A | 10/1981 | Woon et al. |
| 4,317,449 A | 3/1982 | Novakoski |
| 4,333,466 A | 6/1982 | Mathews |
| 4,340,563 A | 7/1982 | Appel et al. |
| 4,381,781 A | 5/1983 | Sciaraffa et al. |
| 4,402,690 A | 9/1983 | Redfern |
| 4,410,324 A | 10/1983 | Sabee |
| 4,413,996 A | 11/1983 | Taylor |
| D272,190 S | 1/1984 | Sneider |
| 4,490,147 A | 12/1984 | Pierce |
| 4,500,316 A | 2/1985 | Damico |
| 4,516,976 A | 5/1985 | Bell |
| 4,560,381 A | 12/1985 | Southwell |
| 4,596,568 A | 6/1986 | Flug |
| 4,610,680 A | 9/1986 | Lafleur |
| 4,610,682 A | 9/1986 | Kopp |
| 4,615,695 A | 10/1986 | Cooper |
| 4,639,254 A | 1/1987 | Legault et al. |
| 4,643,932 A | 2/1987 | Daniels |
| 4,662,875 A | 5/1987 | Hirotsu et al. |
| 4,663,220 A | 5/1987 | Wisneski et al. |
| 4,699,621 A | 5/1987 | Wisneski et al. |
| 4,670,012 A | 6/1987 | Johnson |
| 4,673,402 A | 6/1987 | Weisman et al. |
| 4,680,012 A | 7/1987 | Morley et al. |
| 4,695,278 A | 9/1987 | Lawson |
| 4,699,620 A | 10/1987 | Bernardin |
| 4,699,622 A | 10/1987 | Toussant et al. |
| 4,704,116 A | 11/1987 | Enloe |
| 4,705,513 A | 11/1987 | Sheldon et al. |
| 4,710,190 A | 12/1987 | Wood et al. |
| 4,720,415 A | 1/1988 | Vander Wielen et al. |
| 4,753,649 A | 6/1988 | Pazdernik |
| 4,758,241 A | 7/1988 | Papajohn |
| 4,770,656 A | 9/1988 | Proxmire et al. |
| 4,770,657 A | 9/1988 | Ellis |
| 4,798,603 A | 1/1989 | Meyer et al. |
| 4,834,735 A | 5/1989 | Alemany et al. |
| 4,834,738 A | 5/1989 | Kielpikowski |
| 4,838,885 A | 6/1989 | Bernardin |
| 4,842,596 A | 6/1989 | Kielpikowski et al. |
| 4,846,815 A | 7/1989 | Scripps |
| 4,869,724 A | 9/1989 | Scripps |
| 4,883,480 A | 11/1989 | Huffman et al. |
| 4,884,323 A | 12/1989 | Provost et al. |
| 4,911,702 A | 3/1990 | O'Leary et al. |
| 4,916,005 A | 4/1990 | Loppert et al. |
| 4,936,840 A | 6/1990 | Proxmire |
| 4,938,753 A | 7/1990 | Van Gompel et al. |
| 4,938,757 A | 7/1990 | Van Gompel et al. |
| 4,940,464 A | 7/1990 | Van Gompel et al. |
| 4,963,140 A | 10/1990 | Robertson et al. |
| 4,964,860 A | 10/1990 | Gipson et al. |
| 4,988,344 A | 1/1991 | Reising et al. |
| 4,988,345 A | 1/1991 | Reising et al. |
| 5,013,382 A | 5/1991 | Nalowaniec et al. |
| 5,019,063 A | 5/1991 | Marsan et al. |
| 5,019,072 A | 5/1991 | Polski |
| 5,019,073 A | 5/1991 | Roessler et al. |
| 5,024,672 A | 6/1991 | Widlund |
| 5,026,446 A | 6/1991 | Johnson et al. |
| 5,034,008 A | 7/1991 | Breitkoph |
| 5,046,272 A | 9/1991 | Vogt et al. |
| 5,047,023 A | 9/1991 | Berg |
| 5,055,103 A | 10/1991 | Nomura et al. |
| 5,061,259 A | 10/1991 | Goldman et al. |
| 5,061,262 A | 10/1991 | Chen et al. |
| 5,062,838 A | 11/1991 | Nalowaniec et al. |
| 5,069,678 A | 12/1991 | Yamamoto et al. |
| 5,087,253 A | 2/1992 | Cooper |
| 5,104,116 A | 4/1992 | Pohjola |
| 5,106,385 A | 4/1992 | Allen et al. |
| 5,108,384 A | 4/1992 | Goulait |
| 5,128,193 A | 7/1992 | Anapol et al. |
| 5,133,707 A | 7/1992 | Rogers et al. |
| 5,134,007 A | 7/1992 | Reising et al. |
| 5,147,343 A | 9/1992 | Kellenberger |
| 5,147,347 A | 9/1992 | Huang |
| 5,149,334 A | 9/1992 | Lahman et al. |
| 5,149,335 A | 9/1992 | Kellenberger et al. |
| 5,151,092 A | 9/1992 | Buell et al. |
| 5,156,793 A | 10/1992 | Buell et al. |
| 5,156,902 A | 10/1992 | Pieper et al. |
| 5,163,932 A | 11/1992 | Nomura et al. |
| 5,176,668 A | 1/1993 | Bernardin |
| 5,176,670 A | 1/1993 | Roessler et al. |
| 5,176,671 A | 1/1993 | Roessler et al. |
| 5,188,627 A | 1/1993 | Igaue et al. |
| 5,188,624 A | 2/1993 | Young, Sr. et al. |
| 5,192,506 A | 3/1993 | Kureshy et al. |
| 5,219,646 A | 7/1993 | Gallegher et al. |
| 5,224,405 A | 7/1993 | Pohjola |
| 5,226,992 A | 7/1993 | Morman |
| 5,234,422 A | 8/1993 | Sneller et al. |
| 5,235,515 A | 8/1993 | Ungpiyakul et al. |
| 5,236,429 A | 8/1993 | Widlund |
| 5,242,436 A | 9/1993 | Weil et al. |
| 5,246,431 A | 9/1993 | Minetola et al. |
| 5,246,433 A | 9/1993 | Hasse et al. |
| 5,248,309 A | 9/1993 | Serbiak et al. |
| 5,263,949 A | 11/1993 | Karami et al. |
| 5,272,588 A | 12/1993 | Motoori |
| 5,275,590 A | 1/1994 | Huffman et al. |
| 5,279,604 A | 1/1994 | Robertson et al. |
| 5,286,543 A | 2/1994 | Ungpiyakul et al. |
| 5,288,546 A | 2/1994 | Roessler et al. |
| 5,294,478 A | 3/1994 | Wanek et al. |
| 5,295,988 A | 3/1994 | Muckenfuhs et al. |
| 5,300,057 A | 4/1994 | Miller et al. |
| 5,304,161 A | 4/1994 | Noel et al. |

(56) References Cited

U.S. PATENT DOCUMENTS

| | | |
|---|---|---|
| 5,304,162 A | 4/1994 | Kuen |
| 5,318,555 A | 6/1994 | Siebers et al. |
| 5,320,531 A | 6/1994 | Delizo-Madamba |
| 5,326,612 A | 7/1994 | Goulait |
| 5,330,458 A | 7/1994 | Buell et al. |
| 5,344,691 A | 9/1994 | Hanschen et al. |
| 5,348,547 A | 9/1994 | Payne et al. |
| 5,350,370 A | 9/1994 | Jackson et al. |
| 5,358,500 A | 10/1994 | Lavon |
| 5,364,382 A | 11/1994 | Latimer et al. |
| 5,370,634 A | 12/1994 | Ando et al. |
| 5,370,639 A | 12/1994 | Widlund |
| 5,383,872 A | 1/1995 | Roessler et al. |
| 5,387,208 A | 2/1995 | Ashton et al. |
| 5,399,219 A | 3/1995 | Roessier et al. |
| 5,403,302 A | 4/1995 | Roessier et al. |
| 5,411,497 A | 5/1995 | Tanzer et al. |
| 5,422,172 A | 6/1995 | Wu |
| 5,423,789 A | 6/1995 | Kuen |
| 5,425,377 A | 6/1995 | Caillouette |
| 5,425,725 A | 6/1995 | Tanzer et al. |
| 5,433,715 A | 7/1995 | Tanzer et al. |
| 5,439,458 A | 8/1995 | Noel et al. |
| 5,458,592 A | 10/1995 | Abuto et al. |
| 5,460,622 A | 10/1995 | Dragoo et al. |
| 5,462,541 A | 10/1995 | Bruemmer et al. |
| 5,466,513 A | 11/1995 | Wanek et al. |
| 5,468,236 A | 11/1995 | Everhart et al. |
| 5,486,167 A | 1/1996 | Dragoo et al. |
| 5,489,282 A | 2/1996 | Zehner et al. |
| 5,490,846 A | 2/1996 | Ellis et al. |
| 5,496,298 A | 3/1996 | Kuepper et al. |
| 5,496,428 A | 3/1996 | Sageser et al. |
| 5,501,679 A | 3/1996 | Krueger et al. |
| 5,507,895 A | 4/1996 | Suekane |
| 5,509,914 A | 4/1996 | Osborn, III |
| 5,509,915 A | 4/1996 | Hanson et al. |
| 5,527,300 A | 6/1996 | Sauer |
| 5,527,302 A | 6/1996 | Endres et al. |
| 5,527,304 A | 6/1996 | Buell et al. |
| 5,527,305 A | 6/1996 | Goulait et al. |
| 5,537,722 A | 7/1996 | Neiderhofer et al. |
| 5,540,796 A | 7/1996 | Fries |
| 5,549,591 A | 8/1996 | Landvogt |
| 5,549,592 A | 8/1996 | Fries et al. |
| 5,554,243 A | 9/1996 | Igaue et al. |
| 5,556,394 A | 9/1996 | Roe et al. |
| 5,560,798 A | 10/1996 | Brusky |
| 5,562,646 A | 10/1996 | Goldman et al. |
| 5,562,650 A | 10/1996 | Everett et al. |
| 5,569,229 A | 10/1996 | Rogers |
| 5,571,096 A | 11/1996 | Dobrin et al. |
| 5,575,782 A | 11/1996 | Hasse et al. |
| 5,591,151 A | 1/1997 | Hasse et al. |
| 5,593,399 A | 1/1997 | Tanzer et al. |
| 5,595,567 A | 1/1997 | King et al. |
| 5,595,618 A | 1/1997 | Fries et al. |
| 5,599,335 A | 2/1997 | Goldman et al. |
| 5,599,620 A | 2/1997 | Huskey |
| 5,601,542 A | 2/1997 | Melius et al. |
| 5,603,707 A | 2/1997 | Trombetta et al. |
| 5,605,735 A | 2/1997 | Zehner et al. |
| 5,624,423 A | 4/1997 | Anjur et al. |
| 5,624,428 A | 4/1997 | Sauer |
| 5,624,429 A | 4/1997 | Long et al. |
| 5,628,741 A | 5/1997 | Buell et al. |
| 5,629,063 A | 5/1997 | Gobran |
| 5,634,917 A | 6/1997 | Fujioka et al. |
| 5,647,864 A | 7/1997 | Allen et al. |
| 5,659,538 A | 8/1997 | Stuebe et al. |
| 5,660,666 A | 8/1997 | Dilnik et al. |
| 5,669,894 A | 9/1997 | Goldman et al. |
| 5,669,900 A | 9/1997 | Bullwinkel et al. |
| 5,674,216 A | 10/1997 | Buell et al. |
| 5,681,300 A | 10/1997 | Ahr et al. |
| 5,683,533 A | 11/1997 | Keighley et al. |
| 5,683,794 A | 11/1997 | Wadsworth et al. |
| 5,685,873 A | 11/1997 | Bruemmer et al. |
| 5,690,628 A | 11/1997 | Huskey et al. |
| 5,706,524 A | 1/1998 | Herrin et al. |
| 5,718,698 A | 2/1998 | Dobrin et al. |
| 5,722,127 A | 3/1998 | Coates |
| 5,735,839 A | 4/1998 | Kawaguchi et al. |
| 5,738,669 A | 4/1998 | Suzuki et al. |
| 5,741,241 A | 4/1998 | Guidotti et al. |
| 5,745,922 A | 5/1998 | Rajala et al. |
| 5,746,731 A | 5/1998 | Hisada |
| 5,749,865 A | 5/1998 | Yamamoto et al. |
| 5,749,866 A | 5/1998 | Roe et al. |
| 5,760,080 A | 6/1998 | Wada et al. |
| 5,769,838 A | 6/1998 | Buell et al. |
| 5,772,649 A | 6/1998 | Siudzinski |
| 5,735,840 A | 7/1998 | Kline et al. |
| 5,779,831 A | 7/1998 | Schmitz |
| 5,785,699 A | 7/1998 | Schmitz |
| 5,795,350 A | 8/1998 | Schmitz |
| 5,797,893 A | 8/1998 | Wada et al. |
| 5,817,400 A | 10/1998 | Chen et al. |
| 5,820,617 A | 10/1998 | Igaue et al. |
| 5,830,206 A | 11/1998 | Larsson |
| 5,843,056 A | 12/1998 | Good et al. |
| 5,843,066 A | 12/1998 | Dobrin |
| 5,843,067 A | 12/1998 | Trombetta et al. |
| 5,843,575 A | 12/1998 | Wang et al. |
| 5,849,000 A | 12/1998 | Anjur et al. |
| 5,853,402 A | 12/1998 | Faulks et al. |
| 5,855,574 A | 1/1999 | Kling et al. |
| 5,858,515 A | 1/1999 | Stokes et al. |
| 5,858,535 A | 1/1999 | Wang et al. |
| 5,860,964 A | 1/1999 | Willekens et al. |
| 5,861,074 A | 1/1999 | Wu |
| 5,865,823 A | 2/1999 | Curro |
| 5,876,392 A | 3/1999 | Hisada |
| 5,876,531 A | 3/1999 | Jacobs et al. |
| 5,895,379 A | 4/1999 | Litchholt et al. |
| 5,897,545 A | 4/1999 | Kline et al. |
| 5,897,546 A | 4/1999 | Kido et al. |
| 5,902,296 A | 5/1999 | Fluyeras |
| 5,904,793 A | 5/1999 | Gorman et al. |
| 5,906,604 A | 5/1999 | Ronnberg et al. |
| 5,916,206 A | 6/1999 | Otsubo et al. |
| 5,919,178 A | 7/1999 | Widlund |
| 5,926,926 A | 7/1999 | Kato |
| 5,928,212 A | 7/1999 | Kline et al. |
| 5,940,887 A | 8/1999 | Rajala et al. |
| 5,941,865 A | 8/1999 | Otsubo et al. |
| 5,948,507 A | 9/1999 | Chen et al. |
| 5,957,906 A | 9/1999 | Roe et al. |
| 5,961,506 A | 10/1999 | Guidotti et al. |
| 5,961,761 A | 10/1999 | Heindel et al. |
| 5,971,970 A | 10/1999 | Carlbark et al. |
| 5,977,430 A | 11/1999 | Roe et al. |
| 5,984,911 A | 11/1999 | Siebers et al. |
| 6,007,527 A | 12/1999 | Kawaguchi et al. |
| 6,011,196 A | 1/2000 | Wang et al. |
| 6,017,621 A | 1/2000 | Hilston et al. |
| 6,020,535 A | 2/2000 | Blenke et al. |
| 6,030,373 A | 2/2000 | Van Gompel et al. |
| 6,036,805 A | 3/2000 | Mcnichols |
| 6,045,543 A | 4/2000 | Pozniak et al. |
| 6,049,915 A | 4/2000 | Malowaniec |
| 6,049,916 A | 4/2000 | Rajala et al. |
| 6,051,094 A | 4/2000 | Melbye et al. |
| 6,063,067 A | 5/2000 | Takizawa et al. |
| 6,066,774 A | 5/2000 | Roe |
| 6,068,620 A | 5/2000 | Chmielewski |
| 6,075,178 A | 6/2000 | Wilhelm et al. |
| 6,077,379 A | 6/2000 | Herrin et al. |
| 6,080,909 A | 6/2000 | Osterdahl et al. |
| 6,083,212 A | 7/2000 | Kumasaka |
| 6,093,869 A | 7/2000 | Roe et al. |
| 6,098,203 A | 8/2000 | Rajala et al. |
| 6,107,538 A | 8/2000 | Young et al. |
| 6,107,539 A | 8/2000 | Palumbo et al. |

(56) References Cited

U.S. PATENT DOCUMENTS

| | | |
|---|---|---|
| 6,117,121 A | 9/2000 | Faulks et al. |
| 6,132,411 A | 10/2000 | Huber et al. |
| 6,140,551 A | 10/2000 | Niemeyer et al. |
| 6,142,986 A | 11/2000 | Lord et al. |
| 6,149,590 A | 11/2000 | Smith et al. |
| 6,149,636 A | 11/2000 | Roe et al. |
| 6,156,024 A | 12/2000 | Schulte et al. |
| 6,159,584 A | 12/2000 | Eaton et al. |
| 6,179,820 B1 | 1/2001 | Fernfors |
| 6,183,587 B1 | 2/2001 | Mcfall |
| 6,191,055 B1 | 2/2001 | Boyer, III et al. |
| 6,197,012 B1 | 3/2001 | Mishima et al. |
| 6,198,018 B1 | 3/2001 | Curro |
| 6,203,496 B1 | 3/2001 | Gael et al. |
| 6,213,991 B1 | 4/2001 | Kling et al. |
| 6,213,992 B1 | 4/2001 | Dreier |
| 6,218,593 B1 | 4/2001 | Torimae et al. |
| 6,222,091 B1 | 4/2001 | Beihoffer et al. |
| 6,224,961 B1 | 5/2001 | Hsueh et al. |
| 6,235,011 B1 | 5/2001 | O'Connell |
| 6,240,569 B1 | 6/2001 | Van Gompel et al. |
| 6,241,713 B1 | 6/2001 | Gross et al. |
| 6,255,236 B1 | 7/2001 | Cree et al. |
| 6,258,077 B1 | 7/2001 | Buell et al. |
| 6,260,211 B1 | 7/2001 | Rajala et al. |
| 6,264,643 B1 | 7/2001 | Toyoda |
| 6,266,557 B1 | 7/2001 | Roe et al. |
| 6,287,286 B1 | 9/2001 | Akin et al. |
| 6,287,287 B1 | 9/2001 | Eisberg |
| 6,307,119 B1 | 10/2001 | Cammarota et al. |
| 6,307,120 B1 | 10/2001 | Glaug |
| 6,312,420 B1 | 11/2001 | Sasaki et al. |
| 6,315,765 B1 | 11/2001 | Datta et al. |
| 6,316,688 B1 | 11/2001 | Hammons |
| 6,328,725 B2 | 12/2001 | Femfors |
| 6,359,192 B1 | 3/2002 | Schmidt et al. |
| 6,364,863 B1 | 4/2002 | Yamamoto et al. |
| 6,367,089 B2 | 4/2002 | Van Gompel et al. |
| 6,368,312 B1 | 4/2002 | Otsubo et al. |
| 6,369,292 B1 | 4/2002 | Strack et al. |
| 6,371,951 B1 | 4/2002 | Koczab et al. |
| 6,372,951 B1 | 4/2002 | Ter-Ovanesyan et al. |
| 6,375,646 B1 | 4/2002 | Widlund et al. |
| 6,383,960 B1 | 5/2002 | Everett et al. |
| 6,392,116 B1 | 5/2002 | Beihoffer et al. |
| 6,394,991 B1 | 5/2002 | Takei et al. |
| 6,395,115 B1 | 5/2002 | Popp et al. |
| 6,395,955 B1 | 5/2002 | Roe et al. |
| 6,399,853 B1 | 6/2002 | Roe et al. |
| 6,402,730 B1 | 6/2002 | Malowaniec |
| 6,407,308 B1 | 6/2002 | Roe et al. |
| 6,409,858 B1 | 6/2002 | Popp et al. |
| 6,413,249 B1 | 7/2002 | Turi et al. |
| 6,414,216 B1 | 7/2002 | Malowaniec |
| 6,423,046 B1 | 7/2002 | Fujioka et al. |
| 6,428,525 B1 | 8/2002 | Malowaniec |
| 6,428,526 B1 | 8/2002 | Heindel et al. |
| 6,429,352 B1 | 8/2002 | Herrlein et al. |
| 6,432,098 B1 | 8/2002 | Kline et al. |
| 6,432,243 B1 | 8/2002 | Popp et al. |
| 6,432,248 B1 | 8/2002 | Popp et al. |
| 6,433,244 B1 | 8/2002 | Roe et al. |
| 6,437,213 B1 | 8/2002 | Schmidt et al. |
| 6,437,214 B1 | 8/2002 | Everett et al. |
| 6,440,117 B1 | 8/2002 | Itoh et al. |
| 6,447,497 B1 | 9/2002 | Olson |
| 6,447,628 B1 | 9/2002 | Couillard et al. |
| 6,448,202 B1 | 9/2002 | Miyazawa et al. |
| 6,454,751 B1 | 9/2002 | Olson |
| 6,455,753 B1 | 9/2002 | Giaug et al. |
| 6,458,115 B1 | 10/2002 | Lindqvist et al. |
| 6,461,343 B1 | 10/2002 | Schaefer et al. |
| 6,461,344 B1 | 10/2002 | Widlund et al. |
| 6,463,633 B1 | 10/2002 | Sangani et al. |
| 6,463,663 B1 | 10/2002 | Sangani et al. |
| 6,464,635 B1 | 10/2002 | Jimenez Cerrato et al. |
| 6,465,379 B1 | 10/2002 | Cook et al. |
| D465,842 S | 11/2002 | Magee et al. |
| 6,475,199 B1 | 11/2002 | Gann |
| 6,476,289 B1 | 11/2002 | Buell et al. |
| 6,478,786 B1 | 11/2002 | Glaug et al. |
| 6,479,727 B1 | 11/2002 | Roe |
| 6,481,362 B2 | 11/2002 | Hietpas et al. |
| 6,494,873 B2 | 12/2002 | Karlsson et al. |
| 6,497,032 B2 | 12/2002 | Maxton et al. |
| 6,498,283 B1 | 12/2002 | Wada et al. |
| 6,498,953 B2 | 12/2002 | Roe et al. |
| 6,500,163 B2 | 12/2002 | Rönnberg et al. |
| 6,506,394 B1 | 1/2003 | Yahiaoui et al. |
| 6,506,959 B2 | 1/2003 | Hamajima et al. |
| 6,509,513 B2 | 1/2003 | Glaug et al. |
| 6,513,221 B2 | 2/2003 | Vogt et al. |
| 6,514,187 B2 | 2/2003 | Coenen et al. |
| 6,524,294 B1 | 2/2003 | Hilston et al. |
| 6,533,879 B2 | 3/2003 | Quereshi et al. |
| 6,540,731 B2 | 4/2003 | Magnusson et al. |
| 6,544,244 B1 | 4/2003 | Glaug et al. |
| 6,551,295 B1 | 4/2003 | Schmidt et al. |
| 6,566,578 B1 | 5/2003 | Glaug et al. |
| 6,569,139 B1 | 5/2003 | Datta et al. |
| 6,570,053 B2 | 5/2003 | Roe et al. |
| 6,570,058 B1 | 5/2003 | Fuchs et al. |
| 6,572,595 B1 | 6/2003 | Klemp et al. |
| 6,575,949 B1 | 6/2003 | Waksmundzki et al. |
| 6,575,952 B2 | 6/2003 | Kirk et al. |
| 6,579,275 B1 | 6/2003 | Pozniak et al. |
| 6,582,543 B1 | 6/2003 | Nilsson et al. |
| 6,590,136 B1 | 7/2003 | Young et al. |
| 6,595,976 B2 | 7/2003 | Jitoe et al. |
| 6,596,113 B2 | 7/2003 | Csida et al. |
| 6,602,238 B2 | 8/2003 | Takei et al. |
| 6,605,447 B2 | 8/2003 | Weiss et al. |
| 6,610,904 B1 | 8/2003 | Thomas et al. |
| 6,613,032 B2 | 9/2003 | Ronnberg et al. |
| 6,623,576 B2 | 9/2003 | Mitchell et al. |
| 6,626,881 B2 | 9/2003 | Shingu et al. |
| 6,626,882 B2 | 9/2003 | Hjorth |
| 6,627,394 B2 | 9/2003 | Kritzman et al. |
| 6,630,611 B1 | 10/2003 | Malowaniec |
| 6,632,209 B1 | 10/2003 | Chmielewski |
| 6,635,041 B1 | 10/2003 | Popp et al. |
| 6,635,135 B2 | 10/2003 | Kuen et al. |
| 6,642,431 B1 | 11/2003 | Gellerstedt et al. |
| 6,645,338 B1 | 11/2003 | Sangani et al. |
| 6,646,179 B1 | 11/2003 | Melius et al. |
| 6,646,180 B1 | 11/2003 | Chmielewski |
| 6,648,870 B2 | 11/2003 | Itoh et al. |
| 6,648,871 B2 | 11/2003 | Kusibojoska et al. |
| 6,649,810 B1 | 11/2003 | Minato et al. |
| 6,664,439 B1 | 12/2003 | Arndt et al. |
| 6,669,678 B2 | 12/2003 | Hermansson et al. |
| 6,676,645 B1 | 1/2004 | Bitterhof |
| 6,689,934 B2 | 2/2004 | Dodge, II et al. |
| 6,692,477 B2 | 2/2004 | Gibbs |
| 6,700,036 B2 | 3/2004 | Thomas et al. |
| 6,702,798 B2 | 3/2004 | Christoffel et al. |
| 6,709,423 B1 | 3/2004 | Herrlein et al. |
| 6,710,225 B1 | 3/2004 | Everett et al. |
| 6,713,660 B1 | 3/2004 | Roe et al. |
| 6,719,744 B2 | 4/2004 | Kinnear et al. |
| 6,723,035 B2 | 4/2004 | Franklin et al. |
| 6,723,892 B2 | 4/2004 | Daley |
| 6,726,669 B2 | 4/2004 | Shimada et al. |
| 6,726,670 B2 | 4/2004 | Almberg et al. |
| 6,727,403 B1 | 4/2004 | Ehrnsperger et al. |
| 6,733,483 B2 | 5/2004 | Raufman et al. |
| 6,736,804 B1 | 5/2004 | Robertson et al. |
| 6,740,071 B2 | 5/2004 | Gibbs |
| 6,749,860 B2 | 6/2004 | Tyrrell et al. |
| 6,755,808 B2 | 6/2004 | Balogh et al. |
| 6,761,711 B1 | 7/2004 | Fletcher et al. |
| 6,764,479 B2 | 7/2004 | Kusibojoska et al. |
| 6,770,065 B1 | 8/2004 | Sasaki et al. |
| 6,776,316 B2 | 8/2004 | Van Eperen et al. |

(56) References Cited

U.S. PATENT DOCUMENTS

| | | |
|---|---|---|
| 6,780,173 B2 | 8/2004 | Mishima et al. |
| 6,780,272 B2 | 8/2004 | Wood |
| 6,790,798 B1 | 9/2004 | Suzuki et al. |
| 6,803,496 B2 | 10/2004 | Elder et al. |
| 6,838,591 B2 | 1/2005 | Waksmundzki et al. |
| 6,840,928 B2 | 1/2005 | Datta et al. |
| 6,846,374 B2 | 1/2005 | Popp et al. |
| 6,849,067 B2 | 2/2005 | Fletcher et al. |
| 6,878,223 B2 | 4/2005 | Kuen et al. |
| 6,885,451 B2 | 4/2005 | Vogt et al. |
| 6,888,043 B2 | 5/2005 | Geiser et al. |
| 6,888,044 B2 | 5/2005 | Fell et al. |
| 6,888,143 B2 | 5/2005 | Vogt et al. |
| 6,891,080 B2 | 5/2005 | Minato et al. |
| 6,904,865 B2 | 6/2005 | Klofta et al. |
| 6,911,024 B2 | 6/2005 | Kusibojoska et al. |
| 6,921,647 B2 | 7/2005 | Kritzman et al. |
| 6,923,798 B2 | 8/2005 | Hedén et al. |
| 6,936,129 B2 | 8/2005 | Karami et al. |
| 6,945,968 B2 | 9/2005 | Svensson et al. |
| 6,946,585 B2 | 9/2005 | Brown |
| 6,953,452 B2 | 10/2005 | Popp et al. |
| 6,955,668 B2 | 10/2005 | Almberg et al. |
| 6,972,011 B2 | 12/2005 | Maeda et al. |
| 6,972,012 B1 | 12/2005 | Pozniak et al. |
| 6,981,951 B1 | 1/2006 | Rahe |
| 6,981,968 B2 | 1/2006 | Kusibojoska et al. |
| 6,991,622 B2 | 1/2006 | Nakaoka et al. |
| 6,994,761 B2 | 2/2006 | Klemp et al. |
| 7,000,260 B2 | 2/2006 | Rajala et al. |
| 7,001,368 B2 | 2/2006 | Otsubo |
| 7,002,054 B2 | 2/2006 | Allen et al. |
| 7,018,369 B2 | 3/2006 | Van Gompel et al. |
| 7,044,133 B2 | 5/2006 | Lohrengel et al. |
| 7,048,725 B2 | 5/2006 | Kling et al. |
| 7,060,058 B2 | 6/2006 | Otsubo et al. |
| D527,102 S | 8/2006 | Mills et al. |
| 7,087,046 B2 | 8/2006 | Van Gompel et al. |
| 7,090,667 B2 | 8/2006 | Fell et al. |
| D527,818 S | 9/2006 | Mills et al. |
| 7,156,939 B2 | 1/2007 | Vogt et al. |
| 7,163,745 B2 | 1/2007 | Mangold et al. |
| 7,166,094 B2 | 1/2007 | Glaug et al. |
| 7,172,585 B2 | 2/2007 | Sandin et al. |
| 7,175,910 B2 | 2/2007 | Ehrnsperger et al. |
| 7,195,622 B2 | 3/2007 | Lindström |
| 7,201,743 B2 | 4/2007 | Röhrl |
| 7,204,907 B2 | 4/2007 | Cree et al. |
| 7,217,261 B2 | 5/2007 | Otsubo et al. |
| 7,241,627 B2 | 7/2007 | Wilhelm et al. |
| 7,270,881 B2 | 9/2007 | Schmidt et al. |
| 7,285,178 B2 | 10/2007 | Mischler et al. |
| 7,314,465 B2 | 1/2008 | Van Gompel et al. |
| 7,314,752 B2 | 1/2008 | Kritzman et al. |
| 7,322,967 B2 | 1/2008 | Kondo |
| 7,331,946 B2 | 2/2008 | Shimada et al. |
| 7,332,642 B2 | 2/2008 | Liu |
| 7,344,525 B2 | 3/2008 | Linker, III et al. |
| 7,347,846 B2 | 3/2008 | Hermansson et al. |
| 7,368,027 B2 | 5/2008 | Schneider et al. |
| 7,373,698 B2 | 5/2008 | Erdman et al. |
| 7,378,567 B2 | 5/2008 | Mangold |
| 7,378,568 B2 | 5/2008 | Thomas et al. |
| 7,387,148 B2 | 6/2008 | Vogt et al. |
| 7,396,349 B2 | 7/2008 | Van Himbergen et al. |
| 7,396,585 B2 | 7/2008 | Schmidt et al. |
| 7,402,339 B2 | 7/2008 | Schmidt et al. |
| 7,411,110 B2 | 8/2008 | Sawyer et al. |
| 7,425,242 B2 | 9/2008 | Olsson et al. |
| 7,432,413 B2 | 10/2008 | Roe et al. |
| 7,435,245 B2 | 10/2008 | Wendelstorf et al. |
| 7,438,709 B2 | 10/2008 | Karami et al. |
| 7,449,014 B2 | 11/2008 | Oba et al. |
| 7,455,665 B2 | 11/2008 | Wendelstorf et al. |
| 7,462,754 B2 | 12/2008 | Malowaniec |
| 7,462,756 B2 | 12/2008 | Malowaniec |
| 7,482,505 B2 | 1/2009 | Stupperich et al. |
| 7,488,535 B2 | 2/2009 | Ehrnsperger et al. |
| 7,504,235 B2 | 3/2009 | Song |
| 7,524,313 B2 | 4/2009 | Kline et al. |
| 7,524,449 B2 | 4/2009 | Walsh et al. |
| 7,524,561 B2 | 4/2009 | Schmidt et al. |
| 7,527,618 B2 | 5/2009 | Benning et al. |
| 7,534,237 B2 | 5/2009 | Olson et al. |
| 7,534,481 B2 | 5/2009 | Seth et al. |
| 7,541,177 B2 | 6/2009 | Kritzman et al. |
| 7,544,628 B2 | 6/2009 | Stupperich et al. |
| 7,559,124 B2 | 7/2009 | Poulakis |
| 7,569,039 B2 | 8/2009 | Matsuda et al. |
| 7,569,041 B2 | 8/2009 | Stupperich et al. |
| 7,592,020 B2 | 9/2009 | Boga et al. |
| 7,604,624 B2 | 10/2009 | Veith et al. |
| 7,621,901 B2 | 11/2009 | Karami |
| 7,682,349 B2 | 3/2010 | Popp et al. |
| 7,687,680 B2 | 3/2010 | Fell et al. |
| 7,695,464 B2 | 4/2010 | Fletcher et al. |
| 7,699,825 B2 | 4/2010 | Nakagawa et al. |
| 7,713,371 B2 | 5/2010 | Lohrengel et al. |
| 7,718,021 B2 | 5/2010 | Venturino et al. |
| 7,722,590 B2 | 5/2010 | Tsuji et al. |
| 7,737,324 B2 | 6/2010 | Lavon et al. |
| 7,744,576 B2 | 6/2010 | Busam et al. |
| 7,744,713 B2 | 6/2010 | Blessing et al. |
| 7,749,211 B2 | 7/2010 | Van Gompel et al. |
| 7,750,203 B2 | 7/2010 | Becker et al. |
| 7,758,558 B2 | 7/2010 | Otsubo |
| D624,696 S | 9/2010 | Hsiao |
| 7,794,442 B2 | 9/2010 | Roehrl et al. |
| 7,794,839 B2 | 9/2010 | Schmidt et al. |
| 7,807,861 B2 | 10/2010 | Molander et al. |
| 7,819,851 B2 | 10/2010 | Karlsson |
| 7,837,662 B2 | 11/2010 | Nakagawa et al. |
| 7,838,721 B2 | 11/2010 | Chen |
| 7,838,722 B2 | 11/2010 | Blessing et al. |
| 7,846,383 B2 | 12/2010 | Song |
| 7,851,667 B2 | 12/2010 | Becker et al. |
| 7,851,669 B2 | 12/2010 | Nakagawa et al. |
| 7,857,801 B2 | 12/2010 | Hamall et al. |
| 7,863,498 B2 | 1/2011 | Roe et al. |
| 7,867,213 B2 | 1/2011 | Bandorf et al. |
| 7,906,065 B1 | 3/2011 | Brown et al. |
| 7,918,959 B2 | 4/2011 | Hornung et al. |
| 7,923,597 B2 | 4/2011 | Ponomarenko et al. |
| 7,935,299 B2 | 5/2011 | Walsh et al. |
| 7,943,537 B2 | 5/2011 | Vincent et al. |
| 7,947,467 B2 | 5/2011 | Kritzman et al. |
| 7,947,865 B2 | 5/2011 | Fossum et al. |
| 7,956,236 B2 | 6/2011 | Ponomarenko et al. |
| 7,982,088 B2 | 7/2011 | Roe et al. |
| 7,993,320 B2 | 8/2011 | Hornung et al. |
| 7,994,384 B2 | 8/2011 | Qin et al. |
| 8,016,806 B2 | 9/2011 | Hornung et al. |
| 8,017,827 B2 | 9/2011 | Hundorf et al. |
| 8,025,652 B2 | 9/2011 | Hornung et al. |
| 8,038,662 B2 | 10/2011 | Hornung et al. |
| 8,043,272 B2 | 10/2011 | Long et al. |
| 8,044,257 B2 | 10/2011 | Song |
| 8,083,724 B2 | 12/2011 | Bittner et al. |
| 8,088,967 B2 | 1/2012 | Underhill et al. |
| 8,100,173 B2 | 1/2012 | Hornung et al. |
| 8,138,388 B2 | 3/2012 | Elder et al. |
| 8,142,590 B2 | 3/2012 | Rejala et al. |
| 8,148,598 B2 | 4/2012 | Tsang et al. |
| 8,152,788 B2 | 4/2012 | Beckert et al. |
| 8,158,848 B2 | 4/2012 | Swerev et al. |
| 8,162,913 B2 | 4/2012 | Goates et al. |
| 8,180,603 B2 | 5/2012 | Blessing et al. |
| 8,187,240 B2 | 5/2012 | Busam et al. |
| 8,196,809 B2 | 6/2012 | Thorstensson |
| 8,202,390 B2 | 6/2012 | Malowaniec |
| 8,206,365 B2 | 6/2012 | Norrby |
| 8,206,533 B2 | 6/2012 | Hundorf et al. |
| 8,221,372 B2 | 7/2012 | Kouno et al. |
| 8,221,379 B2 | 7/2012 | Lam et al. |

(56) References Cited

U.S. PATENT DOCUMENTS

| | | |
|---|---|---|
| 8,221,672 B2 | 7/2012 | Brown et al. |
| 8,231,593 B2 | 7/2012 | Nakagawa et al. |
| 8,241,263 B2 | 8/2012 | Mills |
| 8,251,967 B2 | 8/2012 | Malowaniec |
| 8,258,366 B2 | 9/2012 | Wendelstorf |
| 8,263,820 B2 | 9/2012 | Carlucci et al. |
| 8,282,617 B2 | 10/2012 | Kaneda |
| 8,292,865 B2 | 10/2012 | Hutson et al. |
| 8,298,205 B2 | 10/2012 | Norrby et al. |
| 8,303,562 B2 | 11/2012 | Hornung et al. |
| 8,319,005 B2 | 11/2012 | Becker et al. |
| 8,343,296 B2 | 1/2013 | Blessing et al. |
| 8,353,891 B2 | 1/2013 | Hornung et al. |
| 8,454,572 B2 | 6/2013 | Roe et al. |
| 8,454,782 B2 | 6/2013 | Ostertag |
| 8,466,336 B2 | 6/2013 | Carlucci et al. |
| 8,476,173 B2 | 7/2013 | Dovertie et al. |
| 8,496,637 B2 | 7/2013 | Hundorf et al. |
| 8,512,305 B2 | 8/2013 | Dziezok et al. |
| 8,518,539 B2 | 8/2013 | Meyer et al. |
| 8,552,252 B2 | 10/2013 | Hundorf et al. |
| 8,562,580 B2 | 10/2013 | Van Gompel et al. |
| 8,562,581 B2 | 10/2013 | Karami et al. |
| 8,585,666 B2 | 11/2013 | Weisman et al. |
| 8,616,867 B2 | 12/2013 | Brown et al. |
| 8,622,984 B2 | 1/2014 | Rajala et al. |
| 8,663,186 B2 | 3/2014 | Lam et al. |
| 8,668,975 B2 | 3/2014 | Westwood |
| 8,672,915 B2 | 3/2014 | Kuwano et al. |
| 8,708,990 B2 | 4/2014 | Beckert et al. |
| 8,747,379 B2 | 6/2014 | Fletcher et al. |
| 8,771,249 B2 | 7/2014 | Beckert et al. |
| 8,784,398 B2 | 7/2014 | Beckert et al. |
| 8,864,733 B2 | 10/2014 | Koenig et al. |
| 8,920,399 B2 | 12/2014 | Mills |
| 8,946,637 B2 | 2/2015 | Chinn et al. |
| D768,963 S | 10/2016 | Amrikhas et al. |
| 9,750,650 B2 * | 9/2017 | Mills .................... A61F 13/514 |
| 2001/0023341 A1 | 9/2001 | Karami |
| 2001/0025147 A1 | 9/2001 | Roe et al. |
| 2001/0034512 A1 | 10/2001 | Karlsson et al. |
| 2001/0042584 A1 | 11/2001 | Karami et al. |
| 2002/0019615 A1 | 2/2002 | Roe et al. |
| 2002/0045881 A1 | 4/2002 | Kusibojoska et al. |
| 2002/0062117 A1 | 5/2002 | Raufman et al. |
| 2002/0065503 A1 | 5/2002 | Guidotti |
| 2002/0111596 A1 | 8/2002 | Fletcher et al. |
| 2002/0115969 A1 | 8/2002 | Maeda et al. |
| 2002/0123733 A1 | 9/2002 | Itch et al. |
| 2002/0138056 A1 | 9/2002 | Kuen et al. |
| 2002/0138062 A1 | 9/2002 | Kuen et al. |
| 2002/0156441 A1 | 10/2002 | Sawyer et al. |
| 2002/0164658 A1 | 11/2002 | Weiss et al. |
| 2002/0177829 A1 | 11/2002 | Fell et al. |
| 2003/0004490 A1 | 1/2003 | Larsson et al. |
| 2003/0014025 A1 | 1/2003 | Allen et al. |
| 2003/0022581 A1 | 1/2003 | Tsai et al. |
| 2003/0023225 A1 | 1/2003 | Sayama |
| 2003/0055394 A1 | 3/2003 | Gibbs |
| 2003/0097113 A1 | 5/2003 | Molee |
| 2003/0100878 A1 | 5/2003 | Leak et al. |
| 2003/0105446 A1 | 6/2003 | Hutson et al. |
| 2003/0113507 A1 | 6/2003 | Niemeyer et al. |
| 2003/0114808 A1 | 6/2003 | Underhill et al. |
| 2003/0119404 A1 | 6/2003 | Belau et al. |
| 2003/0166293 A1 | 9/2003 | Kritzman et al. |
| 2003/0199843 A1 | 10/2003 | Kato et al. |
| 2004/0044324 A1 | 3/2004 | Swenson et al. |
| 2004/0102755 A1 | 5/2004 | Morman et al. |
| 2004/0122410 A1 | 6/2004 | Itch et al. |
| 2004/0133180 A1 | 7/2004 | Mori et al. |
| 2004/0153046 A1 | 8/2004 | Ito et al. |
| 2004/0158212 A1 | 8/2004 | Ponomarenko et al. |
| 2004/0172000 A1 | 9/2004 | Roe et al. |
| 2004/0243086 A1 | 12/2004 | Van Gompel et al. |
| 2004/0243089 A1 | 12/2004 | Veith et al. |
| 2005/0003143 A1 | 1/2005 | Ducauchuis et al. |
| 2005/0020992 A1 | 1/2005 | Van Gompel |
| 2005/0027279 A1 | 2/2005 | Minato et al. |
| 2005/0075618 A1 | 4/2005 | Kenmochi et al. |
| 2005/0113778 A1 | 5/2005 | Johansson et al. |
| 2005/0131287 A1 | 6/2005 | Kaylor et al. |
| 2005/0131378 A1 | 6/2005 | Sasaki et al. |
| 2005/0143709 A1 | 6/2005 | Lindstrom |
| 2005/0148960 A1 | 7/2005 | Price |
| 2005/0175269 A1 | 8/2005 | Ashton et al. |
| 2005/0228356 A1 | 10/2005 | Lavon et al. |
| 2005/0256494 A1 | 11/2005 | Datta |
| 2005/0256496 A1 | 11/2005 | Benning et al. |
| 2005/0261647 A1 | 11/2005 | Karami et al. |
| 2005/0261650 A1 | 11/2005 | Damaghi et al. |
| 2005/0273067 A1 | 12/2005 | Malowaniec et al. |
| 2006/0024433 A1 | 2/2006 | Blessing et al. |
| 2006/0025733 A1 | 2/2006 | Kikuchi et al. |
| 2006/0036230 A1 | 2/2006 | Mills et al. |
| 2006/0047259 A1 | 3/2006 | Erdman et al. |
| 2006/0058772 A1 | 3/2006 | Karami |
| 2006/0069379 A1 | 3/2006 | Van Gompel et al. |
| 2006/0121811 A1 | 6/2006 | Mangold et al. |
| 2006/0135923 A1 | 6/2006 | Boggs et al. |
| 2006/0135928 A1 | 6/2006 | Karlsson et al. |
| 2006/0135932 A1 | 6/2006 | Abuto et al. |
| 2006/0155254 A1 | 7/2006 | Sanz et al. |
| 2006/0167424 A1 | 7/2006 | Chang et al. |
| 2006/0184149 A1 | 8/2006 | Kasai et al. |
| 2006/0195068 A1 | 8/2006 | Lawando |
| 2006/0212010 A1 | 9/2006 | Roe et al. |
| 2006/0241560 A1 | 10/2006 | Chang et al. |
| 2006/0247596 A1 | 11/2006 | Van Dyke |
| 2006/0258250 A1 | 11/2006 | Mangold et al. |
| 2006/0276765 A1 | 12/2006 | Swerev et al. |
| 2006/0282053 A1 | 12/2006 | Rohrl |
| 2007/0000987 A1 | 1/2007 | Karlsson |
| 2007/0003993 A1 | 1/2007 | Kritzman et al. |
| 2007/0016155 A1 | 1/2007 | Chang et al. |
| 2007/0021728 A1 | 1/2007 | Speak |
| 2007/0038199 A1 | 2/2007 | Erdman et al. |
| 2007/0044903 A1 | 3/2007 | Wisneski et al. |
| 2007/0048497 A1 | 3/2007 | Zhou |
| 2007/0048815 A1 | 3/2007 | Song |
| 2007/0049892 A1 | 3/2007 | Lord et al. |
| 2007/0049896 A1 | 3/2007 | Mills |
| 2007/0066950 A1 | 3/2007 | Nelson |
| 2007/0073260 A1 | 3/2007 | Roe |
| 2007/0073262 A1 | 3/2007 | Babusik et al. |
| 2007/0128589 A1 | 6/2007 | Sanders et al. |
| 2007/0208317 A1 | 9/2007 | Krautkramer et al. |
| 2007/0239131 A1 | 10/2007 | Harmansson et al. |
| 2007/0255246 A1 | 11/2007 | Schneider |
| 2007/0293833 A1 | 12/2007 | Wennerback |
| 2007/0293835 A1 | 12/2007 | Roehrl et al. |
| 2008/0026178 A1 | 1/2008 | Stupperich et al. |
| 2008/0051747 A1 | 2/2008 | Cohen |
| 2008/0086060 A1 | 4/2008 | Kritzman et al. |
| 2008/0103414 A1 | 5/2008 | Song |
| 2008/0108964 A1 | 5/2008 | Edwall |
| 2008/0125735 A1 | 5/2008 | Busam et al. |
| 2008/0134487 A1 | 6/2008 | Hartono |
| 2008/0147031 A1 | 6/2008 | Long et al. |
| 2008/0161767 A1 | 7/2008 | Sandin et al. |
| 2008/0208152 A1 | 8/2008 | Eckstein et al. |
| 2008/0249493 A1 | 10/2008 | Kobayashi et al. |
| 2008/0274014 A1 | 11/2008 | Jumonville et al. |
| 2008/0281286 A1 | 11/2008 | Petersen |
| 2008/0287897 A1 | 11/2008 | Guzman Reyes et al. |
| 2008/0287898 A1 | 11/2008 | Guzman Reyes et al. |
| 2008/0287899 A1 | 11/2008 | Morrell-Schwartz et al. |
| 2008/0312618 A1 | 12/2008 | Hundorf et al. |
| 2008/0312628 A1 | 12/2008 | Hundorf et al. |
| 2008/0312631 A1 | 12/2008 | Okuda |
| 2009/0143757 A1 | 6/2009 | Hornung et al. |
| 2009/0177176 A1 | 7/2009 | Saito |
| 2009/0198205 A1 | 8/2009 | Malowaniec et al. |
| 2009/0275071 A1 | 11/2009 | Brusilovsky et al. |

(56) References Cited

U.S. PATENT DOCUMENTS

| | | |
|---|---|---|
| 2009/0275911 A1 | 11/2009 | Hormung et al. |
| 2009/0299322 A1 | 12/2009 | Faulks et al. |
| 2009/0312736 A1 | 12/2009 | Schroer, Jr. et al. |
| 2009/0326499 A1 | 12/2009 | Veith |
| 2009/0326503 A1 | 12/2009 | Lakso et al. |
| 2010/0051170 A1 | 3/2010 | Nakakado |
| 2010/0063468 A1 | 3/2010 | Lehto et al. |
| 2010/0065199 A1 | 3/2010 | Hormung et al. |
| 2010/0076390 A1 | 3/2010 | Norrby et al. |
| 2010/0108251 A1 | 5/2010 | Malowaniec |
| 2010/0136707 A1 | 6/2010 | Kritzman et al. |
| 2010/0163161 A1 | 7/2010 | Gilgenbach et al. |
| 2010/0168705 A1 | 7/2010 | Stabelfeldt et al. |
| 2010/0198178 A1 | 8/2010 | Litvay |
| 2010/0234820 A1 | 9/2010 | Tsai |
| 2010/0290948 A1 | 11/2010 | Song |
| 2010/0292663 A1 | 11/2010 | Lavon et al. |
| 2010/0318055 A1 | 12/2010 | Hornung et al. |
| 2011/0071488 A1 | 3/2011 | Kuwano et al. |
| 2011/0098668 A1 | 4/2011 | Thorson et al. |
| 2011/0123775 A1 | 5/2011 | Westwood |
| 2001/0144610 | 6/2011 | Karlson et al. |
| 2011/0130275 A1 | 6/2011 | Weisman et al. |
| 2011/0146892 A1 | 6/2011 | Ostertag |
| 2011/0160692 A1 | 6/2011 | Wilkes et al. |
| 2011/0208140 A1 | 8/2011 | Roe et al. |
| 2011/0208142 A1 | 8/2011 | Roe et al. |
| 2012/0028777 A1 | 2/2012 | Knecht |
| 2012/0053552 A1 | 3/2012 | Van Gompel et al. |
| 2012/0065607 A1 | 3/2012 | Konig et al. |
| 2012/0165777 A1 | 6/2012 | Beckert et al. |
| 2012/0172828 A1 | 7/2012 | Koenig et al. |
| 2012/0310193 A1 | 12/2012 | Ostertag |
| 2013/0144245 A1 | 6/2013 | Roe |
| 2013/0211365 A1 | 8/2013 | Rajala et al. |
| 2013/0277154 A1 | 10/2013 | Fritz et al. |
| 2013/0281957 A1 | 10/2013 | Fritz et al. |
| 2013/0296739 A1 | 11/2013 | Schultz |
| 2013/0345667 A1 | 12/2013 | Nelson et al. |
| 2014/0046286 A1 | 2/2014 | Homann et al. |
| 2014/0121487 A1 | 5/2014 | Faybishenko et al. |
| 2015/0011958 A1 | 1/2015 | Yoshioka |
| 2015/0297419 A1 | 10/2015 | Nelson |
| 2015/0297421 A1 | 10/2015 | Nelson et al. |
| 2015/0297423 A1 | 10/2015 | Nelson et al. |

FOREIGN PATENT DOCUMENTS

| | | |
|---|---|---|
| GB | 2135568 A | 9/1984 |
| JP | 2000060899 A | 2/2000 |
| WO | 9843574 A1 | 10/1998 |
| WO | 9923985 A1 | 5/1999 |
| WO | 9948452 A1 | 9/1999 |
| WO | 2006017718 A1 | 2/2006 |

\* cited by examiner

ABSORBENT ARTICLE

CROSS-REFERENCE TO RELATED APPLICATION

This application is a Continuation of U.S. patent application Ser. No. 14/551,587, now U.S. Pat. No. 9,750,650, filed Nov. 24, 2014, which is a Continuation of U.S. patent application Ser. No. 13/755,583, now U.S. Pat. No. 8,920,399, filed Jan. 31, 2013, which is a Continuation of U.S. patent application Ser. No. 12/565,562, filed Sep. 23, 2009, now U.S. Pat. No. 8,419,703, which is a Continuation of U.S. patent application Ser. No. 11/341,015, now U.S. Pat. No. 8,241,263, filed Jan. 27, 2006, which claims the benefit of U.S. Provisional Application No. 60/712,023, filed Aug. 26, 2005, all of which are herein incorporated by reference in their entireties.

FIELD OF THE INVENTION

The present invention relates to an absorbent article and, more specifically, to using target strips and visual sizing indicators on the absorbent article to advise when to downsize an adult incontinent brief or disposable diaper to achieve a proper fit.

BACKGROUND OF THE INVENTION

Adult incontinent briefs, disposable diapers, and other absorbent articles are designed to absorb and contain liquid and other discharges from the human body to prevent body and clothing soiling. These absorbent articles typically have an outer layer of thin plastic film such as polyethylene, which may be reinforced at the areas where adhesive closure tabs are adhered during fastening of the absorbent article around a wearer. The reinforcement frequently may be a stronger plastic film that is adhesively attached to the outer layer and may be known as a target strip.

Often, an ill-fitting absorbent article is chosen for a wearer. One reason for the ill-fit is due to the fact that the size determination of absorbent articles is often based on a single criteria such as a wearer's weight, hip circumference, or waist circumference. Thus, other relevant factors such as age, height, thigh circumference, and rise are not taken into account. Alternatively, a wearer or caregiver may purposely choose a larger sized absorbent article under the mistaken belief that it will have a greater absorbency and hence be more beneficial. In reality, however, an oversized absorbent article may slip, slide, sag, or droop, any of which may cause discomfort and/or leakage.

Unlike determining that an absorbent article is too small for a wearer, determining that an absorbent article is too large for a wearer can be difficult and problematic. It is evident when an absorbent article is too small for a wearer because adhesive closure tabs, typically located on a back portion of the absorbent article, will not reach the target strips located on the front portion of the absorbent article, thus making it impossible to secure the absorbent article to the wearer. In contrast, when an absorbent article is too large for a wearer, the back portion may be wrapped around the wearer's waist, and the adhesive closure tabs may be adhered anywhere on the absorbent article, including portions located outside of the target strips. Because wearers of absorbent articles are often very young children or elderly persons, the wearers may be unable to walk or move freely and therefore may be unlikely to notice the absorbent article sagging or drooping. Moreover, the wearer may not be able to effectively communicate to his or her caregiver that the absorbent article is too large. In other cases, the ill-fit may be relatively subtle, leading the wearer to mistakenly believe that a proper fitting brief was chosen.

Downsizing an absorbent article has several benefits to the wearer. First, downsizing to an absorbent article that provides a better fit is likely to reduce leakage, since the smaller absorbent article will be less likely to slip, slide, sag, or droop. Moreover, downsizing an absorbent article may be more cost effective. Larger-sized absorbent articles are typically more expensive than smaller-sized absorbent articles of comparable absorbency. This is due to the fact that larger absorbent articles require the use of more absorbent materials and are thus more costly to manufacture. Often, a case of larger-sized absorbent articles will cost the same as smaller-sized absorbent articles but will contain considerably fewer absorbent articles.

Therefore, there exists a need to indicate to a wearer or caregiver when an absorbent article should be downsized.

SUMMARY OF THE INVENTION

According to one embodiment, an absorbent article comprises a first portion having at least two target strips located on opposite edges of the first portion, at least one visual sizing indicator positioned on the first portion of the article between the at least two target strips, a middle portion contoured inwards such that an hourglass shape is formed, and a second portion having at least two fasteners located on opposite edges of the second portion. The absorbent article is formed of several layers including a moisture-impervious outer layer, an inner layer substantially co-extensive with the outer layer, and a filler interposed between the inner layer and the outer layer.

According to another embodiment of the present invention, a method of determining that an absorbent article is too large for a wearer comprises the act of positioning the absorbent article on the wearer, the absorbent article comprising a first portion including at least two target strips positioned on opposite edges of the first portion and at least one visual sizing indicator located between the at least two target strips, and a second portion including at least two fasteners positioned on opposite edges of the second portion. The method further comprises the act of pulling the opposite edges of the second portion in opposite directions such that the second portion is stretched to form a snug fit to the wearer. The method further comprises attaching the at least two fasteners to the first portion. The method further comprises determining whether the absorbent article should be downsized based on whether the at least two fasteners overlap the at least one visual sizing indicator when attached to the first portion.

According to another embodiment of the present invention, an absorbent article comprises a first portion having at least two target strips located on opposite edges of the first portion, at least one visual sizing indicator positioned on the first portion of the article between the at least two target strips, a middle portion contoured inwards such that an hourglass shape is formed, and a second portion having at least two fasteners located on opposite edges of the second portion.

The above summary of the present invention is not intended to represent each embodiment or every aspect of the present invention. The detailed description and Figures will describe many of the embodiments and aspects of the present invention.

BRIEF DESCRIPTION OF THE DRAWINGS

The foregoing and other advantages of the invention will become apparent upon reading the following detailed description and upon reference to the drawings.

FIG. 2 illustrates a cross-section generally taken through section line 2-2 of the brief of FIG. 1a.

FIG. 3b illustrates a left side view of the brief of FIG. 3a.

FIG. 4b illustrates a left side view of the brief of FIG. 4a.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

The present invention is directed to an absorbent article having target strips and indicators to advise a wearer or caregiver when the absorbent article is too large for the wearer. Although the remainder of the disclosure herein will be directed toward an adult incontinent brief, it is to be understood that the invention may also be implemented on other absorbent articles, including disposable diapers.

Figure 1A:
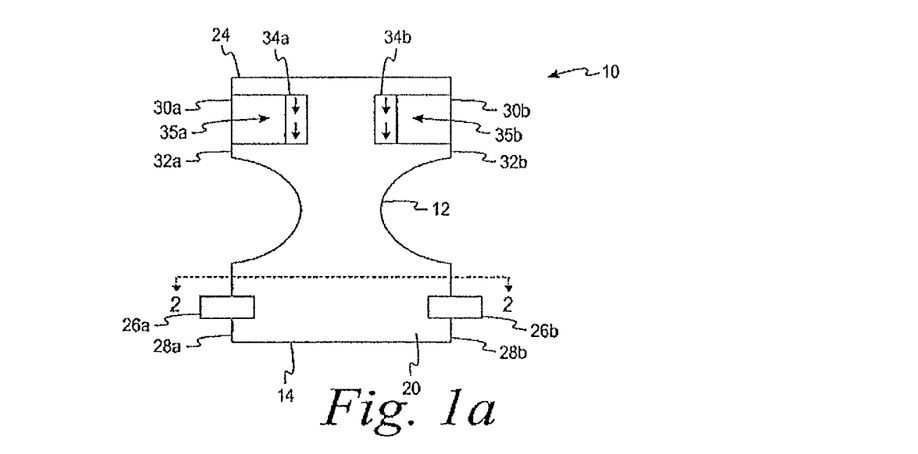
FIG. 1a illustrates a top view of an outer layer of an open adult incontinent brief, according to one embodiment of the present invention.
Figure 2:
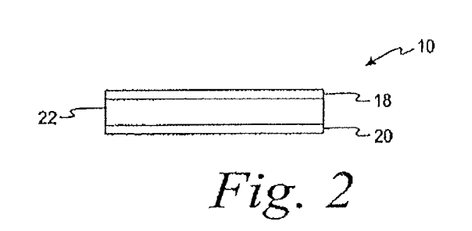

Turning first to FIG. 1a, the outer layer 20 of an adult incontinent brief 10 according to one embodiment of the present invention is illustrated. The brief 10 is of substantially rectangular configuration. In this embodiment, the middle portion 12 is contoured in an "hourglass" configuration to fit around a wearer's thighs when the brief 10 is secured to the wearer. The brief 10 also includes a front portion 24 and a back portion 14. The brief 10 generally consists of several layers, as shown in FIG. 2. FIG. 2 is a cross-sectional view of the brief 10 generally along section line 2-2 shown in FIG. 1a. The brief 10 includes an inner layer 18, which faces a wearer when the brief 10 is secured to the wearer. The inner layer 18 may be comprised of a nonwoven topsheet. The brief 10 also includes a moisture-impervious outer layer 20, which faces away from a wearer when the brief 10 is secured to the wearer. This outer layer 20 is substantially co-extensive with the inner layer 18. The outer layer 20 may be made of any material suitable to minimize fluids and other discharge from escaping the brief, including polyethylene and/or breathable poly. A filler layer 22 is positioned between the inner layer 18 and the outer layer 20. The absorbency of the brief generally may range from about 250 cc to about 2,000 cc. The filler layer 22 may be composed of any materials suitable for absorbing fluids and discharge, including super absorbent polymer (SAP) and fluff.

Figure 3A:
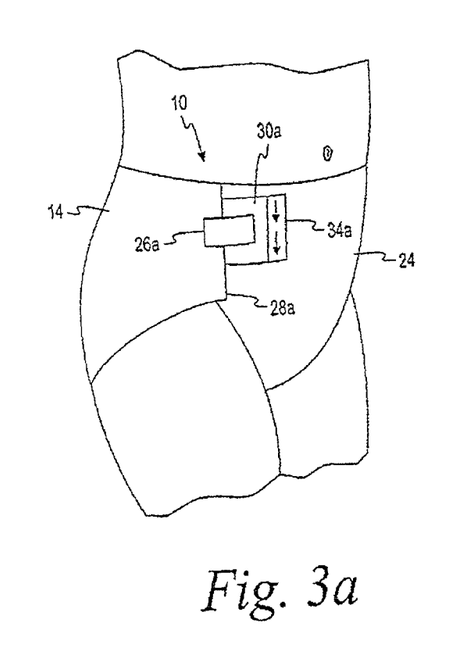
FIG. 3a illustrates a right side view of the brief of FIG. 1a, the brief being secured and fit-appropriate to a wearer.
Figure 3B:
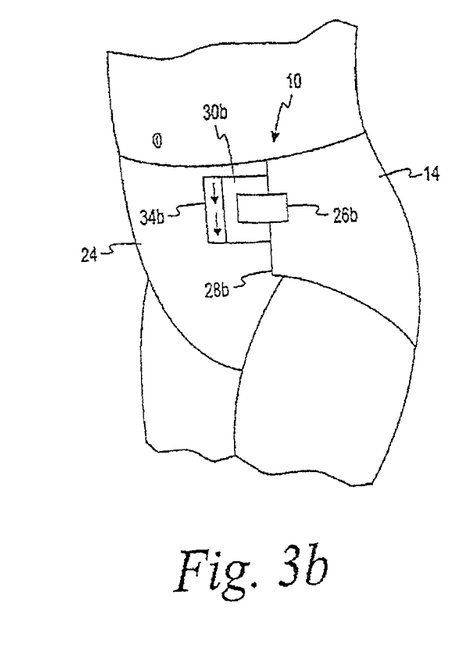

Referring back to FIG. 1a, a top view of the outer layer 20 of the brief 10 is shown. The brief 10 includes features designed for securing the brief 10 to a wearer. For example, the brief 10 has fasteners 26a, 26b positioned on opposite side edges 28a, 28b of the brief 10. In the embodiment of FIG. 1a, the fasteners 26a, 26b are positioned on the back portion 14 of the brief 10. The fasteners 26a, 26b extend over the side edges 28a, 28b of the back portion 14, thus allowing the fasteners 26a, 26b to contact and attach to the front portion 24 when the brief 10 is folded and positioned on a wearer, as shown in FIGS. 3a and 3b. The types of fasteners 26a, 26b may include pressure sensitive adhesive tape or other adhesive materials, tab members having adhesive on one side, Velcro®, safety pins, hook and loop type latches, and/or other means suitable for attaching the back portion 14 to the front portion 24 such that the brief 10 may be secured to a wearer. Adult incontinent briefs may include at least two fasteners per side to ensure both a tight fit around the wearer's waist as well as a tight or sealed gasket in the wearer's crotch area to prevent leakage.

The brief 10 of the present invention also includes target strips 30a, 30b. The target strips 30a, 30b are areas where the fasteners 26a, 26b are to be attached to the front portion 24 during securing of the brief 10 around a wearer. The target strips 30a, 30b may include a frontal tape landing zone(s) or adhesive label imprinted material(s). A frontal tape landing zone may include a section of tape positioned on the front portion 24 of the brief 10 to which the fastener(s) 26a, 26b may be fastened. The frontal tape landing zone may include an adhesive label imprinted material. The adhesive label imprinted material may be imprinted with text, characters, graphics, fabrics, other indicia, or a combination thereof. The target strips 30a, 30b may comprise an area of reinforced material, such as a stronger plastic film or biaxially oriented polypropylene (BOPP). The area of reinforced material is frequently comprised of a stronger plastic film that is adhesively attached to the outer layer 20. The area of reinforced material may be particularly useful in embodiments where the type of fastener(s) 26a, 26b includes an adhesive tape or the like so that the fastener(s) 26a, 26b may be removed from the area of reinforced material without damaging the brief 10. The target strips 30a, 30b may include other distinct physical characteristics to enhance the ability to secure the fasteners 26a, 26b to the brief 10, thereby decreasing the likelihood of the fasteners 26a, 26b becoming unfastened. The target strips 30a, 30b may, for example, generally have a width of approximately 165 mm and a length of approximately 165 mm for size large, extra-large (XL), and double extra-large (XXL) briefs. Size small, medium, and regular briefs may, for example, generally have a width of approximately 165 mm and a length of approximately 140 mm. It is contemplated that the target strips 30a, 30b may also have other lengths and widths. The target strips 30a, 30b shown in this embodiment are generally rectangular in shape. It is contemplated that they may take the form of other shapes, including, but not limited to, squares, polygons, or circles.

The target strips 30a, 30b are located on the portion of the brief 10 generally opposite the fasteners 26a, 26b. In the embodiment of FIG. 1a, the target strips 30a, 30b are located at or near the side edges 32a, 32b of the front portion 24. It is contemplated that the fasteners 26a, 26b may be positioned on the front portion 24 of the brief 10, and the target strips 30a, 30b may be positioned on the back portion 14 of the brief 10. However, it may be more convenient to place the fasteners 26a, 26b on the back portion 14 of the brief 10 so that the fasteners 26a, 26b may be secured to the front portion 24, thus making it unnecessary to reach behind the wearer, who is often lying down, in order to secure the fasteners 26a, 26b. In some embodiments, the target strips 30a, 30b are visually distinct from other areas of the brief 10 so that the wearer or caregiver may readily recognize the areas where the fasteners 26a, 26b should optimally attach to the brief 10. For example, the target strips 30a, 30b may include text, characters, graphics, fabrics, or a combination thereof, including happy faces, green lights, or other indicia, different from the rest of the brief 10 and suitable for indicating that a proper fit has been achieved.

Figure 1B:
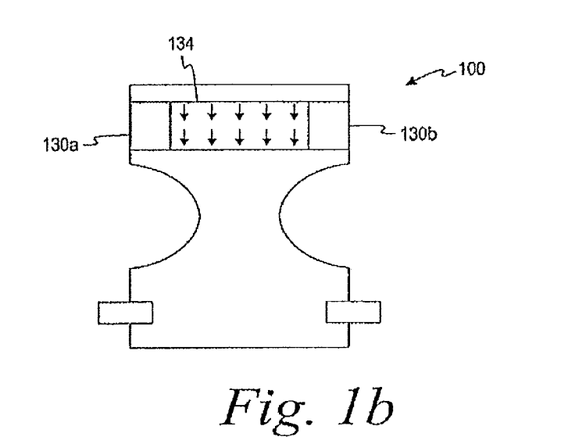
FIG. 1b illustrates a top view of an outer layer of an open adult incontinent brief, according to another embodiment of the present invention.

The brief 10 also includes visual sizing indicators 34a, 34b. As shown in FIG. 1a, the visual sizing indicators 34a, 34b may be located adjacent to the target strips 30a, 30b on the inner sides 35a, 35b of the target strips 30a, 30b opposite the side edges 32a, 32b of the brief 10. In another embodiment, the visual sizing indicators 34a, 34b may be located on the target strips 30a, 30b in an area adjacent to the inner sides 35a, 35b. As demonstrated in the embodiment of FIG. 1b, it is further contemplated that a single visual sizing indicator 134 may be positioned adjacent to and between the target strips 130a, 130b, thereby connecting the first target strip 130a to the second target strip 130b of the brief 100.

Referring back to FIG. 1a, the purpose of the visual sizing indicators 34a, 34b is to indicate to a wearer or a caregiver securing the brief 10 to the wearer that the brief 10 is too large and should be downsized. FIGS. 3a and 3b show the brief 10 of FIG. 1a being fit-appropriate and positioned on a wearer. In order to secure the brief 10 to the wearer, the side edges 28a, 28b of the back portion 14 are grasped and pulled in opposite directions, laterally and outwardly, stretching the back portion 14 so that it lies flat and snug against the wearer. Each of the side edges 28a, 28b should be pulled with generally the same amount of force so that the brief 10 remains positioned generally evenly and symmetrically on the wearer. The side edges 32a, 32b of the front portion 24 are also pulled so that the front portion 24 lies flat and snug against the wearer's abdomen. The brief 10 is then secured to the wearer by securing the fasteners 26a, 26b to a section of the front portion 24 of the brief 10 located as far around the wearer's waist as the fasteners 26a, 26b will comfortably reach so that the side edges 28a, 28b of the back portion 14 overlap the side edges 32a, 32b of the front portion 24.

If, when the brief 10 is secured to a wearer, the fasteners 26a, 26b attach to the front portion 24 of the brief 10 in an area overlapping the target strips 30a, 30b, as shown in FIGS. 3a and 3b, the correct size brief has been chosen. FIG. 3a shows the right side of the brief 10 fastened to a wearer where the brief 10 is secured and fit-appropriate to the wearer. FIG. 3b shows the left side of the brief 10 of FIG. 3a. The proper fit of the brief 10 may be illustrated to the wearer or caregiver through the target strips 30a, 30b distinguishable by the text, characters, graphics, fabrics, other indicia, or combinations thereof of the target strips 30a, 30b.

Figure 4A:
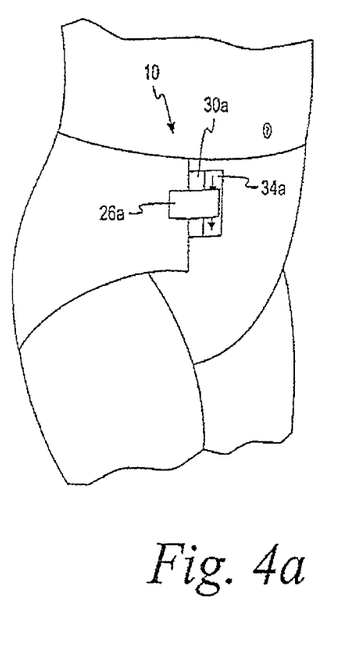
FIG. 4a illustrates a right side view of the brief of FIG. 1a, the brief being secured and ill-fitted to a wearer.
Figure 4B:
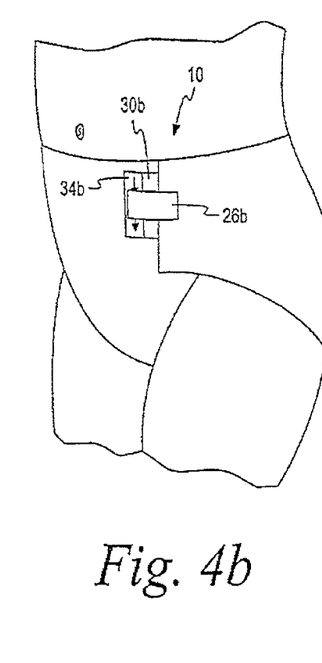
Figure 5:
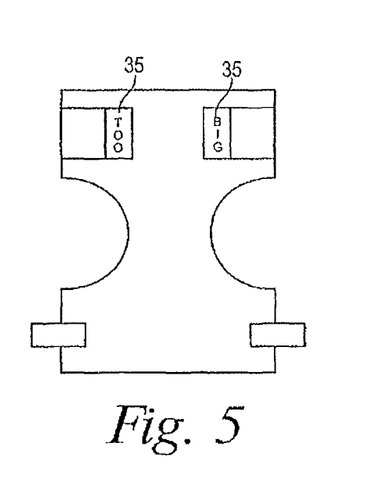
FIGS. 5-7 illustrate top views of outer layers of open adult incontinent briefs, according to other embodiments of the present invention.
Figure 6:
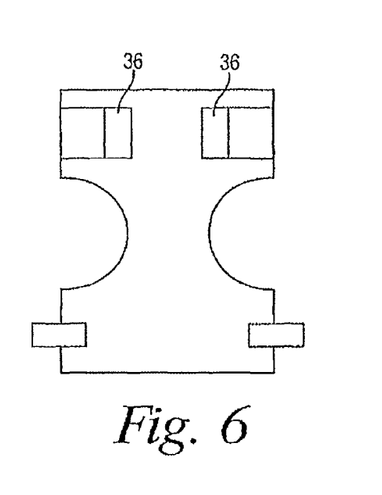
Figure 7:
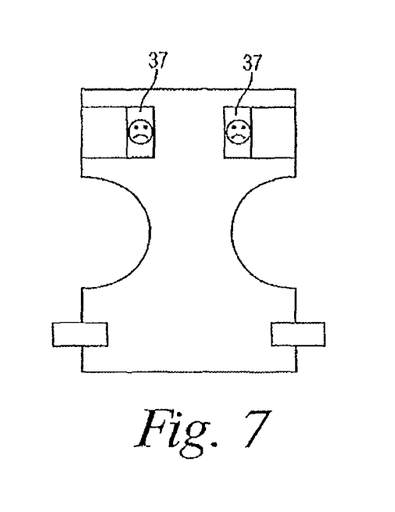

If, when the brief 10 is secured to a wearer, the fasteners 26a, 26b attach to the front portion 24 of the brief 10 in the area overlapping the visual sizing indicators 34a, 34b, as shown in FIGS. 4a and 4b, the brief 10 is too large for the wearer. FIG. 4a shows the right side of a brief 10 fastened to a wearer where the brief is secured but ill-fitted to the wearer. FIG. 4b shows the left side of the brief 10 of FIG. 4a. The visual indicators 34a, 34b may include indicia such as, but not limited to, text (see text 35 of FIG. 5), characters, graphics, fabrics (see fabric 36 of FIG. 6), other indicia, or combinations thereof, to indicate to the wearer or caregiver that the brief 10 is too large and should be downsized. In the embodiment shown, arrows pointing downward are used to suggest downsizing the brief 10. Other indicia may include, but is not limited to sad faces graphics (see sad faces graphic 37 of FIG. 7), red lights or color, or other characters suitable for indicating that an ill-fit has been achieved. The visual sizing indicators 34a, 34b should be distinguishable from the target strips 30a, 30b, thus making it evident to the wearer or caregiver that the brief 10 is too large for the wearer because the fasteners 26a, 26b are being secured to the brief 10 in an area outside the target strip 30a, 30b and within the area of the visual sizing indicators 34a, 34b.

According to alternative embodiment A, an absorbent article comprises a first portion having at least two target strips located on opposite ends of the first portion, at least one visual sizing indicator positioned on the first portion of the article between the at least two target strips, a middle portion contoured inwards such that an hourglass shape is formed, and a second portion having at least two fasteners located on opposite edges of the second portion, wherein the absorbent article is formed of several different layers, including a moisture-impervious outer layer, an inner layer substantially co-extensive with the outer layer, and a filler interposed between the inner layer and the outer layer.

According to alternative embodiment B, the absorbent article of alternative embodiment A, wherein the absorbent article is an adult incontinent brief.

According to alternative embodiment C, the article of alternative embodiment A, wherein the absorbent article is a disposable diaper.

According to alternative embodiment D, the absorbent article of alternative embodiment A, wherein the at least two fasteners are tab members having adhesive on one side.

According to alternative embodiment E, the absorbent article of alternative embodiment A, wherein the first portion is a front portion and the second portion is a back portion when the absorbent article is positioned on a wearer.

According to alternative embodiment F, the absorbent article of alternative embodiment A, wherein the at least two target strips are comprised of a reinforced material.

According to alternative embodiment G, the absorbent article of alternative embodiment A, wherein the at least two target strips include text, characters, graphics, fabrics, or a combination thereof.

According to alternative embodiment H, the absorbent article of alternative embodiment A, wherein the at least one visual sizing indicator includes arrows, text, characters, graphics, fabrics, or a combination thereof.

According to alternative embodiment I, a method of determining that an absorbent article is too large for a wearer comprises the acts of positioning the absorbent article on the wearer, the absorbent article comprising a first portion including at least two target strips positioned on opposite edges of the first portion and at least one visual sizing indicator located between the at least two target strips, and a second portion including at least two fasteners positioned on opposite edges of the second portion, pulling the opposite edges of the second portion in opposite directions such that the second portion is stretched to form a snug fit to the wearer, attaching the at least two fasteners to the first portion, and determining whether the absorbent article should be downsized based on whether the fasteners overlap the at least one visual sizing indicator when attached to the first portion.

According to alternative embodiment J, the method of alternative embodiment I, wherein the at least two fasteners overlapping the at least two target strips indicate that the absorbent article is an appropriate fit for the wearer.

According to alternative embodiment K, the method of alternative embodiment I, wherein the at least two fasteners overlapping the at least one visual sizing indicator indicate that the absorbent article should be downsized for the wearer.

According to alternative embodiment L, the method of alternative embodiment I, wherein the absorbent article is an adult incontinent brief.

According to alternative embodiment M, the method of alternative embodiment I, wherein the absorbent article is a disposable diaper.

According to alternative embodiment N, the method of alternative embodiment I, wherein the at least two fasteners are tab members having adhesive on one side.

According to alternative embodiment O, the method of alternative embodiment I, wherein the first portion is a front portion and the second portion is a back portion when the absorbent article is positioned on the wearer.

According to alternative embodiment P, the method of alternative embodiment I, wherein the at least two target strips are comprised of a reinforced material.

According to alternative embodiment Q, the method of alternative embodiment I, wherein the at least two target strips include text, characters, graphics, fabrics, or a combination thereof.

According to alternative embodiment R, the method of alternative embodiment I, wherein the at least one visual sizing indicator includes arrows, text, characters, graphics, fabrics, or a combination thereof.

According to alternative embodiment S, an absorbent article comprises a first portion having at least two target strips located on opposite ends of the first portion, at least one visual sizing indicator positioned on the first portion of the article between the at least two target strips, a middle portion contoured inwards such that an hourglass shape is formed, and a second portion having at least two fasteners located on opposite edges of the second portion.

According to alternative embodiment T, an absorbent article of alternative embodiment S, wherein the at least one visual sizing indicator is two visual sizing indicators, the two visual sizing indicators being formed on the at least two target strips.

According to alternative embodiment U, the absorbent article of alternative embodiment S, wherein the at least one visual sizing indicator is two visual sizing indicators, the two visual sizing indicators being positioned adjacent to the at least two target strips.

According to alternative embodiment V, an absorbent article comprises a first portion having at least two target strips located on opposite ends of the first portion, at least one visual sizing indicator positioned on the first portion of the article between the at least two target strips, a middle portion contoured inwards such that an hourglass shape is formed, and a second portion having at least two fasteners located on opposite edges of the second portion, wherein the article is formed of several layers including a moisture-impervious outer layer, an inner layer substantially co-extensive with the outer layer, and a filler interposed between the inner layer and the outer layer.

According to alternative embodiment W, the article of alternative embodiment V, wherein the at least two target strips include at least one character, graphic, fabric, text or a combination thereof.

According to alternative embodiment X, the article of alternative embodiment V, wherein the at least one visual sizing indicator includes at least one arrow, text, character, graphic, fabric, or a combination thereof.

According to alternative embodiment Y, a method of determining that an absorbent article is too large for a wearer comprises the acts of positioning the article on the wearer, the article comprising a first portion including at least two target strips positioned on opposite edges of the first portion and at least one visual sizing indicator located between the at least two target strips, and a second portion including at least two fasteners positioned on opposite edges of the second portion, pulling the opposite edges of the second portion in opposite directions such that the second portion is stretched to form a snug fit to the wearer, attaching the at least two fasteners to the first portion, and determining whether the article should be downsized based on whether the at least two fasteners overlap the at least one visual sizing indicator when attached to the first portion.

According to alternative embodiment Z, the method of alternative embodiment Y, wherein the at least two target strips include at least one character, graphic, fabric, text, or a combination thereof.

According to alternative embodiment AA, the method of alternative embodiment Y, wherein the at least one visual sizing indicator includes at least one arrow, text, character, graphic, fabric, or a combination thereof.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention, which is set forth in the following claims.

The invention claimed is:
1. An absorbent article comprising:
a moisture-impervious outer layer;
an inner layer substantially co-extensive with the outer layer;
a filler interposed between the inner layer and the outer layer;
a rear portion having a first rear side with a first rear side edge and a second rear side with a second rear side edge, the rear portion comprising:
  a first fastener attached to the first rear side and extending beyond the first rear side edge, and
  a second fastener attached to the second rear side and extending beyond the second rear side edge; and
a front portion comprising:
  a first side edge,
  a first target strip on an outside surface of the front portion adjacent to the first side edge,
  a second side edge,
  a second target strip on an outside surface of the front portion adjacent to the second edge and spaced apart from the first target strip, and
  a sizing indicator positioned between the first target strip and the second target strip, wherein the sizing indicator is visually distinct from the first target strip and the second target strip;
wherein the first fastener overlaps with and attaches to the first target strip without overlapping the sizing indicator and the second fastener overlaps with and attaches to the second target strip without overlapping the sizing indicator when a correctly sized brief is positioned on the wearer; and wherein the first fastener overlaps with the sizing indicator and secures the article on the wearer when the absorbent article is oversized for the wearer.

2. The absorbent article of claim 1, wherein the first target strip comprises a first fabric.

3. The absorbent article of claim 2, wherein the sizing indicator comprises a second fabric, visually distinct from the first fabric.

4. The absorbent article of claim 3, wherein the second target strip comprises the first fabric.

5. The absorbent article of claim 1, wherein the first target strip comprises a physical characteristic to enhance the ability to secure the first fastener.

6. The absorbent article of claim 1, wherein the first target strip comprises a generally rectangular shape.

7. The absorbent article of claim 1, wherein the first target strip comprises a generally square shape.

8. The absorbent article of claim 1, wherein the first target strip comprises a polygon shape.

9. The absorbent article of claim 1, wherein the first target strip comprises a generally circular shape.

10. The absorbent article of claim 1, wherein the first target strip and second target strip each comprise a first material, and the sizing indicator comprises a second material distinct from the first material.

11. An absorbent article comprising:
a moisture-impervious outer layer;
an inner layer substantially co-extensive with the outer layer;
a filler interposed between the inner layer and the outer layer;
a rear portion having a first rear side with a first rear side edge and a second rear side with a second rear side edge, the rear portion comprising:
a first fastener attached to the first rear side and extending beyond the first rear side edge, and
a second fastener attached to the second rear side and extending beyond the second rear side edge; and
a front portion comprising:
a first side edge,
a first target strip on an outside surface of the front portion adjacent to the first side edge,
a second side edge,
a second target strip on an outside surface of the front portion adjacent to the second edge and spaced apart from the first target strip, and
a sizing indicator positioned between the first target strip and the second target strip;
wherein the first target strip and second target strip each comprise a first material, and the sizing indicator comprises a second material distinct from the first material
wherein the first fastener overlaps with and attaches to the first target strip without overlapping the sizing indicator and the second fastener overlaps with and attaches to the second target strip without overlapping the sizing indicator when a correctly sized brief is positioned on the wearer; and
wherein the first fastener overlaps with the sizing indicator and secures the article on the wearer when the absorbent article is oversized for the wearer.

12. The absorbent article of claim 11, wherein the sizing indicator is visually distinct from the first target strip and the second target strip.

13. The absorbent article of claim 11, wherein the first target strip has a polygon shape and the second target strip has a polygon shape.

14. The absorbent article of claim 11, wherein the front portion comprises a first section covered by the sizing indicator.

15. The absorbent article of claim 14, wherein the front portion comprises a second section not covered by the sizing indicator.

16. The absorbent article of claim 14, wherein the sizing indicator is visually distinguishable from the second section of the front portion.

* * * * *